United States Patent
Fonseca et al.

(10) Patent No.: US 11,166,676 B2
(45) Date of Patent: Nov. 9, 2021

(54) REAL-TIME KIDNEY MONITORING MEDICAL DEVICE

(71) Applicants: Marina I. Adrianzen Fonseca, Mill Valley, CA (US); Saisanjana Kalagara, Tempe, AZ (US); Regine Rosas, St. Louis, MO (US); Cynthia Hale-Phillips, New Haven, CT (US)

(72) Inventors: Marina I. Adrianzen Fonseca, Mill Valley, CA (US); Saisanjana Kalagara, Tempe, AZ (US); Regine Rosas, St. Louis, MO (US); Cynthia Hale-Phillips, New Haven, CT (US)

( * ) Notice: Subject to any disclaimer, the term of this patent is extended or adjusted under 35 U.S.C. 154(b) by 834 days.

(21) Appl. No.: 15/838,205

(22) Filed: Dec. 11, 2017

(65) Prior Publication Data

US 2019/0175113 A1    Jun. 13, 2019

(51) Int. Cl.
| | |
|---|---|
| *A61B 5/026* | (2006.01) |
| *A61B 5/0215* | (2006.01) |
| *A61B 5/00* | (2006.01) |
| *A61B 5/20* | (2006.01) |
| *A61B 5/022* | (2006.01) |
| *A61B 90/00* | (2016.01) |

(52) U.S. Cl.
CPC ............ *A61B 5/6884* (2013.01); *A61B 5/026* (2013.01); *A61B 5/0215* (2013.01); *A61B 5/02241* (2013.01); *A61B 5/201* (2013.01); *A61B 5/6876* (2013.01); *A61B 5/6885* (2013.01); *A61B 5/7278* (2013.01); *A61B 5/746* (2013.01); *A61B 2090/064* (2016.02); *A61B 2562/0247* (2013.01); *A61B 2562/164* (2013.01); *A61B 2562/166* (2013.01)

(58) Field of Classification Search
CPC . A61B 5/6884; A61B 5/0215; A61B 5/02241; A61B 5/026; A61B 5/201; A61B 5/6876; A61B 5/6885; A61B 5/7278; A61B 5/746; A61B 2090/064; A61B 2562/0247; A61B 2562/164; A61B 2562/166
USPC ........ 600/481, 483, 485, 486, 488, 490–499
See application file for complete search history.

(56) References Cited

U.S. PATENT DOCUMENTS

| | | | |
|---|---|---|---|
| 7,007,551 B2 * | 3/2006 | Zdeblick .............. | A61B 5/0215 73/715 |
| 7,013,734 B2 * | 3/2006 | Zdeblick .............. | A61B 5/0215 73/715 |

(Continued)

*Primary Examiner* — Navin Natnithithadha
(74) *Attorney, Agent, or Firm* — Vierra Magen Marcus LLP

(57) ABSTRACT

This medical device measures blood flow rate through the renal artery after a kidney transplant in real time. The device utilizes a force sensing resistor (FSR) to detect the amount of blood and the given blood pressure at any instantaneous point in time. The FSR wraps around the renal artery after transplantation and should remain connected for five to seven days for optimal kidney blood flow and kidney functioning detection. This will be achieved by measuring the flow rate, estimating blood pressure, and beats per minute this device should alert doctors if irregular kidney function should occur for fast and immediate surgical or bedside intervention. Our goal is to detect post-transplant kidney rejection in real-time. The device is biocompatible and sterile, easily removed from the renal artery, and smaller than 5 mm in diameter.

4 Claims, 7 Drawing Sheets

(56) References Cited

U.S. PATENT DOCUMENTS

| | | | | |
|---|---|---|---|---|
| 7,028,550 B2* | 4/2006 | Zdeblick | A61B 5/0215 | 73/715 |
| 7,066,031 B2* | 6/2006 | Zdeblick | A61B 5/0215 | 73/715 |
| 7,073,387 B2* | 7/2006 | Zdeblick | A61B 5/0215 | 73/715 |
| 7,147,604 B1* | 12/2006 | Allen | A61B 5/0031 | 600/549 |
| 7,162,303 B2* | 1/2007 | Levin | A61N 5/00 | 607/44 |
| 7,284,441 B2* | 10/2007 | Zdeblick | A61B 5/0215 | 73/753 |
| 7,398,688 B2* | 7/2008 | Zdeblick | G01L 9/045 | 73/700 |
| 7,647,115 B2* | 1/2010 | Levin | A61B 18/1492 | 607/44 |
| 7,762,138 B2* | 7/2010 | Zdeblick | A61B 5/0215 | 73/700 |
| 8,131,372 B2* | 3/2012 | Levin | A61B 18/04 | 607/44 |
| 8,150,518 B2* | 4/2012 | Levin | A61B 18/1492 | 607/44 |
| 8,246,639 B2* | 8/2012 | Kassab | A61B 17/122 | 606/158 |
| 8,760,154 B2* | 6/2014 | Giddings | G01B 7/24 | 324/209 |
| 8,880,186 B2* | 11/2014 | Levin | A61N 1/40 | 607/62 |
| 9,066,661 B2* | 6/2015 | Giddings | G01L 1/125 | |
| 9,131,856 B2* | 9/2015 | Giddings | G01B 7/24 | |
| 9,629,560 B2* | 4/2017 | Joseph | A61B 5/6879 | |
| 9,743,983 B2* | 8/2017 | Levin | A61B 18/04 | |
| 9,757,192 B2* | 9/2017 | Levin | A61N 1/0551 | |
| 9,907,611 B2* | 3/2018 | Levin | A61M 5/1723 | |
| 9,968,790 B2* | 5/2018 | Toth | A61B 5/4839 | |
| 9,999,356 B2* | 6/2018 | Giddings | A61B 5/02108 | |
| 10,179,028 B2* | 1/2019 | Levin | A61N 5/00 | |
| 10,226,633 B2* | 3/2019 | Toth | A61B 5/042 | |
| 10,335,043 B2* | 7/2019 | Jain | A61B 5/0031 | |
| 10,342,439 B2* | 7/2019 | Giddings | A61B 5/02108 | |
| 10,413,200 B2* | 9/2019 | Joseph | A61B 5/686 | |
| 10,602,936 B2* | 3/2020 | Joseph | A61B 5/076 | |
| 2003/0216792 A1* | 11/2003 | Levin | A61M 5/142 | 607/48 |
| 2005/0160823 A1* | 7/2005 | Zdeblick | G01L 9/0055 | 73/715 |
| 2005/0160824 A1* | 7/2005 | Zdeblick | G01L 9/0042 | 73/715 |
| 2005/0160825 A1* | 7/2005 | Zdeblick | A61N 1/36564 | 73/715 |
| 2005/0160826 A1* | 7/2005 | Zdeblick | G01L 9/0055 | 73/715 |
| 2005/0160827 A1* | 7/2005 | Zdeblick | G01L 9/0055 | 73/715 |
| 2005/0273014 A1* | 12/2005 | Gianchandani | G01F 1/56 | 600/505 |
| 2006/0137457 A1* | 6/2006 | Zdeblick | A61N 1/36564 | 73/715 |
| 2007/0151348 A1* | 7/2007 | Zdeblick | A61N 1/36564 | 73/708 |
| 2009/0013791 A1* | 1/2009 | Zdeblick | A61B 5/0215 | 73/700 |
| 2009/0105631 A1* | 4/2009 | Kieval | A61M 1/367 | 604/9 |
| 2012/0079887 A1* | 4/2012 | Giddings | G01B 7/24 | 73/779 |
| 2012/0109164 A1* | 5/2012 | Kassab | A61B 17/122 | 606/151 |
| 2014/0207006 A1* | 7/2014 | Giddings | A61B 5/02108 | 600/485 |
| 2014/0207007 A1* | 7/2014 | Giddings | G01B 7/24 | 600/485 |
| 2015/0224326 A1* | 8/2015 | Toth | A61B 5/0205 | 600/301 |
| 2015/0338292 A1* | 11/2015 | Giddings | A61B 5/021 | 600/485 |
| 2016/0287094 A1* | 10/2016 | Joseph | A61B 5/14551 | |
| 2016/0287174 A1* | 10/2016 | Joseph | A61B 5/6876 | |
| 2017/0065186 A1* | 3/2017 | Joseph | A61B 5/0215 | |
| 2017/0065188 A1* | 3/2017 | Jain | A61B 5/14542 | |
| 2017/0360312 A1* | 12/2017 | Joseph | A61B 5/14551 | |
| 2018/0200524 A1* | 7/2018 | Toth | A61B 5/24 | |
| 2018/0256035 A1* | 9/2018 | Giddings | G01L 1/125 | |
| 2019/0151670 A1* | 5/2019 | Toth | A61B 5/02007 | |
| 2019/0175113 A1* | 6/2019 | Fonseca | A61B 5/026 | |

* cited by examiner

| # Pulses | Threshold | Value | Flow Rate (mL/min) |
|---|---|---|---|
| 18 | 0.1 | 1.49712 | 504 |

First Order Model: $Y = 17.5 (X_0) - 17.5 (X_1) + 17.5 (X_2)$

| Blood Volume | Distance | Error |
|---|---|---|
| -1 | -1 | 0 |
| -1 | -1 | 0 |
| -1 | 1 | 84 |
| -1 | 1 | 56 |
| 1 | -1 | 0 |
| 1 | -1 | 0 |
| 1 | 1 | 0 |
| 1 | 1 | 0 |

REAL-TIME KIDNEY MONITORING MEDICAL DEVICE

BACKGROUND

For patients with end-stage renal disease, kidney transplants are one of the best treatment options. They are long-lasting, convenient when compared to continuous dialysis treatments, and result in a generally good quality of life. Only about 16,000 kidney transplants are done every year in the U.S., while there are approximately 100,000 patients on the transplant waiting list. The biggest factor for this relatively small percentage of transplants done is the dearth of available organs that are suitable for the procedure. Usually, only kidneys that come from generally young and healthy donors are accepted. However, in order to increase the number of transplants done every year, marginal organs, or those from older donors or those with slightly impaired kidneys, are increasingly being used for transplantation.

One of the problems with marginal organs is that they are more likely to have delayed graft function. This phenomenon describes the kidneys that do not start working immediately after transplantation, approximately 30% of all kidneys transplanted. Instead these kidneys start working within a week post-transplant. This means that patients must be kept in the hospital for an extra week until the organ starts working. Another 2% of total kidneys transplanted never work at all due to conditions like thrombosis, a blood clot in the renal artery that blocks blood flow. The problem is that during this week of hospital stay, doctors do not know whether the kidney simply has delayed function or if there is a more serious problem, such as a clot formation. Without this information, they are not able to act quickly if there is a problem. This clinical need must be addressed to improve patient outcomes post-transplant and is especially important as the use of marginal organs increases.

BRIEF DESCRIPTION OF THE DRAWINGS

Like-numbered reference numbers in the drawings refer to common components in the different figures.

DETAILED DESCRIPTION

Figure 1:
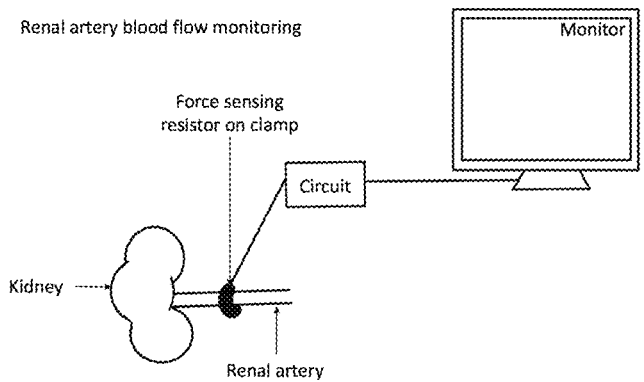
FIG. 1 depicts the real-time kidney monitoring device measuring blood flow through the renal artery using a force sensing resistor on a clamp.

To improve patient outcomes post-transplant a real-time kidney monitoring device is proposed. This medical device measures blood flow rate in real-time through the renal artery after a kidney transplant. The device utilizes a force sensing resistor (FSR) to detect the amount of blood and the given blood pressure at any instantaneous point in time. The FSR wraps around the renal artery after transplantation and should remain connected for five to seven days for optimal kidney blood flow and kidney functioning detection. This will be achieved by measuring the flow rate, estimating blood pressure, and beats per minute. This device will alert doctors if irregular kidney function should occur for fast and immediate surgical or bedside intervention. Thus, the proposed device detects post-transplant kidney rejection in real-time. The device is biocompatible and sterile, easily removed from the renal artery, and smaller than 5 mm in diameter.

The proposed real-time kidney monitoring device is easy to use; easy to attach to renal artery after transplant before patient is sewn back up; easy to read and understand real-time data regarding blood flow through the kidney; easily removable at the bedside, non-invasively; capable of being used by nurses to constantly monitor kidney function; has as few risks as possible; and cheap enough to have at every bedside post-transplant.

In clinical settings, there are currently three types of testing that are used to evaluate kidney function post-transplant. To begin, blood and urine tests are performed daily until the patient has left the hospital. Some of the variables measured in these tests are complete blood count, white blood cell count, bicarbonate levels, and urine content (with respect to blood, protein, and bacteria). One specific test, a plasma clearance test based on measurements of PAH (para-aminohippurate) levels, uses PAH concentration in the urine, PAH concentration in arterial blood, and the urine flow rate to quantitatively estimate the renal plasma flow, a predictive measure of kidney function. If the blood or urine tests indicate concerningly abnormal kidney function, the next level of testing that is done is the ultrasound. An ultrasound allows the doctor to know whether or not there is blood flow through the kidney and includes a resistive index measurement that is correlated with peak velocity of blood flow in the kidney. This test is only used very rarely, however, and requires a trained technician and at least 24 hours before the results are available.

The limitation of these currently used methods is that they do not monitor kidney function in real-time and almost always include a 24-hour delay, which impairs the ability of the physicians to act quickly if there is a problem. Furthermore, the most commonly used tests, the blood and urine tests, are only indirect predictors of kidney function and can sometimes be misleading. Though ultrasounds are much more accurate as they actually show the organ, they are rarely done and are more expensive.

There are also other methods of monitoring kidney function post-transplant that are currently in the experimental stages. One of these techniques is an implantable, photonics-based sensor that continuously monitors blood flow following kidney transplant surgery. The advantages of this system are that it is small enough to be implanted for renal applications and it provides a real-time output of information about kidney function. A major disadvantage of this design, however, is that it requires another invasive procedure to remove, which can be a major hurdle for physicians and patients that just recently had an operation.

The proposed real-time kidney monitoring medical device measures blood flow rate through the renal artery after a kidney transplant in real time. The device utilizes a force sensing resistor (FSR) to detect the amount of blood and the given blood pressure at any instantaneous point in time. The FSR wraps around the renal artery after transplantation and should remain connected for five to seven days for optimal kidney blood flow and kidney functioning detection. This will be achieved by measuring the flow rate, estimating blood pressure, and measuring beats per minute. This device will alert doctors if irregular kidney function should occur for fast and immediate surgical or bedside intervention. One goal is to detect post-transplant kidney rejection in real-time. The device is biocompatible and sterile, easily removed from the renal artery, and smaller than 5 mm in diameter.

Figure 6:
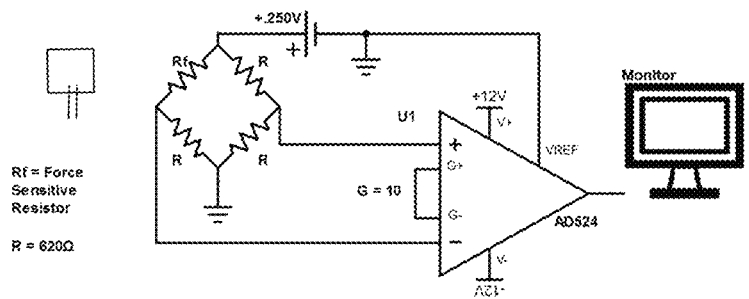
FIG. 6 is a circuit diagram of the real-time kidney monitoring device that is configured to measure renal blood flow, where Rf represents the FSR attached to a clamp. The circuit includes a Wheatstone bridge to integrate our FSR.
Figure 14:
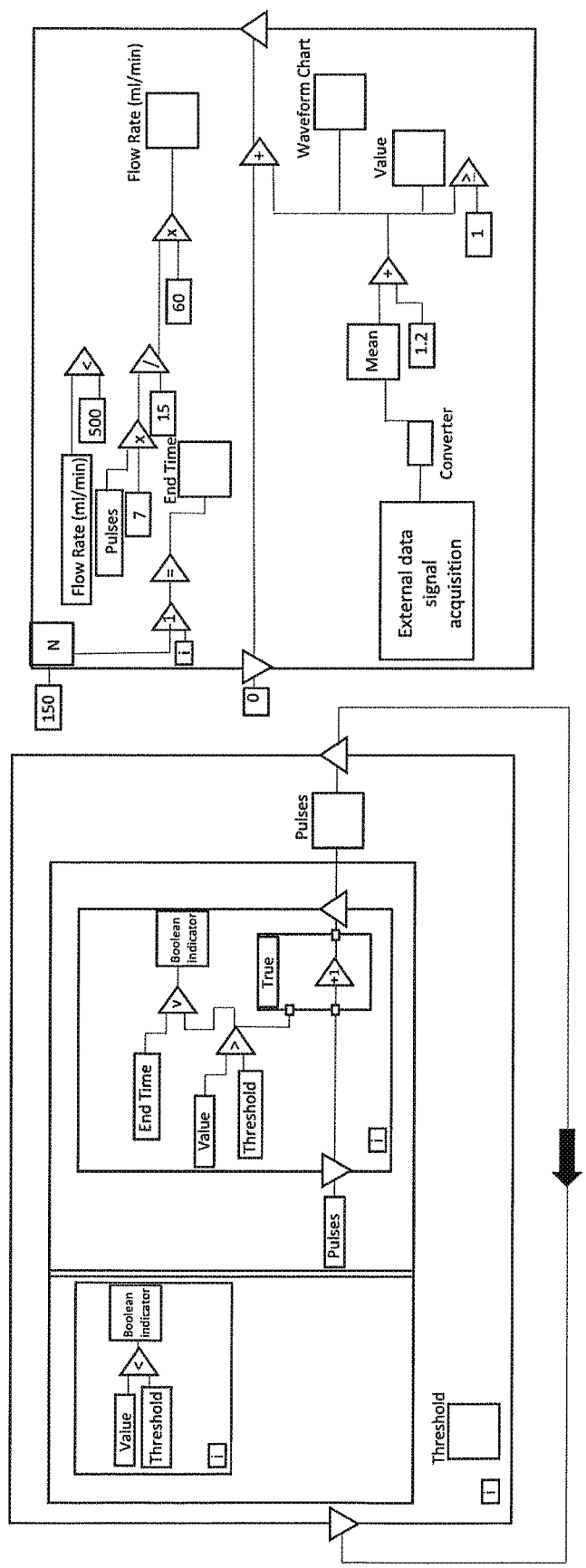
FIG. 14 depicts receiving electrical signals representing pressure changes in the renal artery and calculating total pulses through the renal artery. The system also determines the flow rate of blood based on renal pulses which in normal adults is about 500 milliliters per minute.

In order to measure flow rate, we will use a pressure transducer that is attached to the renal artery with a clamp. We will process the signal from the pressure transducer using a circuit that outputs a signal to a computer running Labview, a signal processing software. A monitor is connected to the computer, and the monitor configured to provide alerts if irregular kidney function should occur. The Labview code will count the peaks and calculate flow rate, which is displayed on a monitor. The three major components of our prototype testing are: (1) the pressure transducer, (2) the clamping mechanism, and (3) the renal artery. This is shown in FIG. 1, which depicts a force sensing resistor wrapped around and/or clamped to the renal artery of the kidney. The force sensing resistor is electrically connected to a circuit (electrical circuit). The circuit (ie a monitoring circuit) is connected to and outputs to a computer that has a monitor. One example of a suitable circuit is depicted in FIG. 6. FIG. 14 depicts receiving electrical signals representing pressure changes in the renal artery and calculating total pulses through the renal artery. The system also determines the flow rate of blood based on renal pulses which in normal adults is about 500 milliliters per minute. The system can monitor change in pressure at the renal artery to count heart beats and blood flow. For example, each change from low pressure to high pressure indicates another heart beat with blood flow through the renal artery. Lack of such change in pressure indicates that there is not sufficient blood flow through the renewal artery, therefore, the monitor displays a warning that there is not sufficient blood flow.

Figure 5:
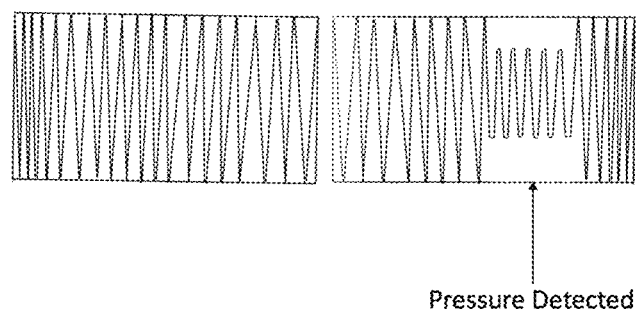
FIG. 5 is a graph demonstrating pressure detection using the FSR at 3 Volts.

In order to measure changes in pressure, we use a pressure transducer that acts as a force sensitive resistor. The resistance of the resistor decrease as force is applied. FIG. 5 is a graph depicting the change in resistance when pressure is detected.

Figure 7:
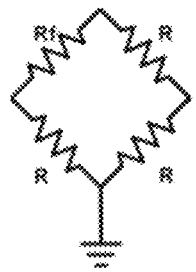
FIG. 7 is a schematic diagram of the Wheatstone bridge part of the circuit which is used to equilibrate the FSR.

The pressure transducer is placed in a wheatstone bridge with three other resistors with the same resistances. FIG. 7 is a schematic diagram of the Wheatstone bridge part of the circuit which is used to equilibrate the FSR. FIG. 6 is a circuit diagram of the real-time kidney monitoring device that is configured to measure renal blood flow, where Rf represents the FSR attached to a clamp. The circuit includes the Wheatstone bridge to integrate the FSR. Two legs of the circuit are sent to the two inputs of an operational amplifier which amplifies the difference between the two input voltages. The output voltage is sent to a Labview Virtual Instrument (VI) which processes and outputs the signal to calculate any of the blood flow metrics described herein (e.g., flow rate, blood pressure, beats per time interval, etc.).

In order to process the pressure transducer signal, we adjusted the following variables:

TABLE 1

Design Variables and Sensitivities based on resistance, gain, and voltage

| Design Variable | Determination of Sensitivity |
| --- | --- |
| R - Resistance of the three unchanging resistors in the wheatstone bridge | The resistors chosen is as close to the resting resistance of the pressure transducer as possible. Therefore, when the pressure transducer has no applied force, there will be little to no difference in voltage between the two legs of the wheatstone bridge. With resistances as close to the resistance of the pressure transducer, the circuit will be sensitive to small forces applied to it. |
| Excitation voltage to the wheatstone bridge | Excitation voltage must be great enough to sense changes in voltage between the two legs, but must not be too much to saturate the maximum input voltage that the computer can take (10 V). |
| Gain of instrumentation amplifier | Gain of our instrumentation amplifier can be 10, 100, or 1000. Correct gain must be used to analyze the signal without saturation. |

Resistors for the wheatstone bridge were initially set to 1 MΩ, the resistance of the pressure transducer when subjected to a 200 g mass, the lightest weight that would cause a change in resistance. When placed in the wheatstone bridge, the pressure transducer was subjected to light taps and pulses from our dialysis tubing and the resistors were further adjusted to best recognize these pressure changes. The final resistors used were 620 kΩ.

The maximum voltage that the computer's data acquisition card could take was 10V. Therefore, the excitation voltage and gain were adjusted to make sure that pulses would never exceed 10V while still being amplified enough to distinguish pulses. The final excitation voltage was 0.250V and the instrumentation amplifier gain was set to 10.

Constraints for the prototype were determined during testing. Voltages from 0.250 V to 6.0 V were tested. We determined that the best voltages were in the lower range, closer to 0.250 V, it gave us the most consistent data with higher sensitivity to decreases in blood flow and blood pressure. Throughout testing we used resistances that ranged from 640 k-ohm to 100 M-ohm. Since our resistances were so high and our voltages values were so low we can use Ohm's law to determine the current of the system. Humans can take current, but currents that exceed 100 to 200 mA are lethal. Ohm's Law is V=IR. We can determine that the currents we used ranged from 0.25 uA to 6 uA which is a lot lower than the current needed to shock a person and even lower than the lethal limit.

TABLE 2

Current ranges based on varied resistances and voltages

| Currents Tested | Voltage (V) | Resistance (Ohm) | Current (μA) |
|---|---|---|---|
| Lowest | .250 | 1,000,000 | .25 |
| Intermediate 1 | .250 | 640,000 | .39 |
| Intermediate 2 | 6 | 1,000,000 | 6 |
| Highest | 6 | 640,000 | 9.38 |

Given that the radius of the renal artery is about 2 mm we can determine the maximum dimensions of the pressure transducer. Finding the circumference of the renal artery gives us the maximum length transducer. We have 2*PI*radius so we get about 12.56 mm as a constraint for length. To determine the other dimension we would have to measure and average renal artery length after transplantation, so further testing would be required.

We determined the highest current a person can take and the lowest voltage at which the device can still function. The following is our budget proposal for our prototype. In the future we need to scale down our product while still minimizing the cost.

Without pricing constraints, a smaller pressure transducer would be used. The pressure transducer would be flexible and printed on silicone so as to be biocompatible. Size-wise, it would conform to half the circumference of the renal artery which has a diameter of 2 mm. We would like for the pressure transducer to have greater sensitivity for more accurate readings and consistency.

The Labview code takes the raw voltage signal from the pressure transducer and converts it to signal that can be correlated to blood pulsing through the artery. Each pulsing cycle from the heart has two distinct phases: systolic and diastolic. During the systolic stage, the pressure in the artery is high, corresponding to high pressure on the transducer. During the diastolic stage the pressure drops which is also detected on the transducer. For arterial normal function, the degree which the pressure drops and the time that the pressure remains low during the diastolic stage is well defined. Extended periods of low pressure or an extreme drop in pressure of the renal artery indicate that the kidney is undergoing thrombosis and immediate surgical intervention is required.

TABLE 3

| code parameters | |
|---|---|
| Sample rate of data acquisition | Sample rate must be high enough to provide continuous readings from the pressure transducer but is constrained by the sample rate that the computer can allow. |
| Number of samples - Number of samples that would be averaged to create one point on our graph | Large number of samples means a less noisy reading, however, might obscure fast drops or peaks that will get averaged with the rest of the data. Number of samples must be adjusted to reduce noise while still providing a continuous reading. |
| Threshold - minimum value that would count as a "peak" | The threshold determines what counts as a peak/pulse. Higher thresholds discriminate noise, but might miss lower amplitude peaks. Optimization |

TABLE 3-continued

| code parameters | |
|---|---|
| | of this variable is further explored in Section 3.3. |

Figure 8:
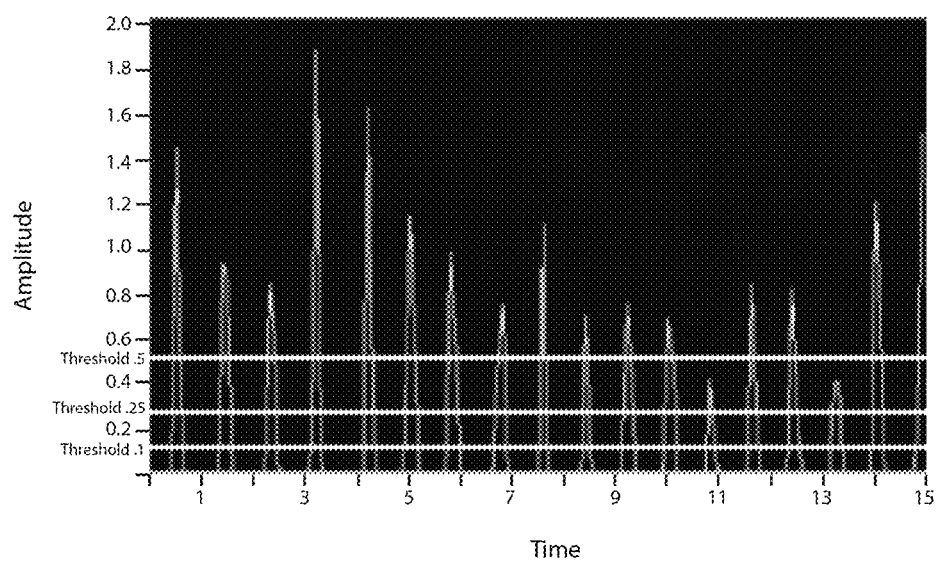
FIG. 8 is a waveform graph of initial testing of pressure transistor to set signal threshold for calculating flow rate.
Figure 9:
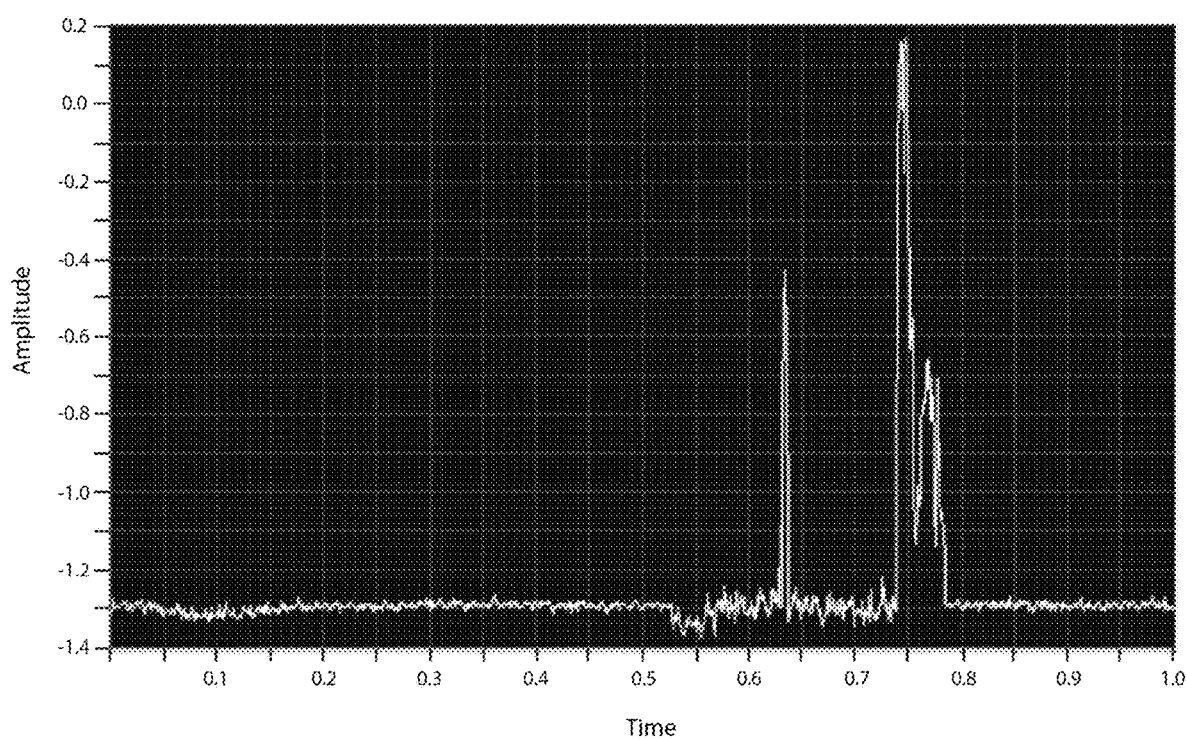
FIG. 9 is a waveform graph of pressure transistor signal processing.
Figures 10, 11:
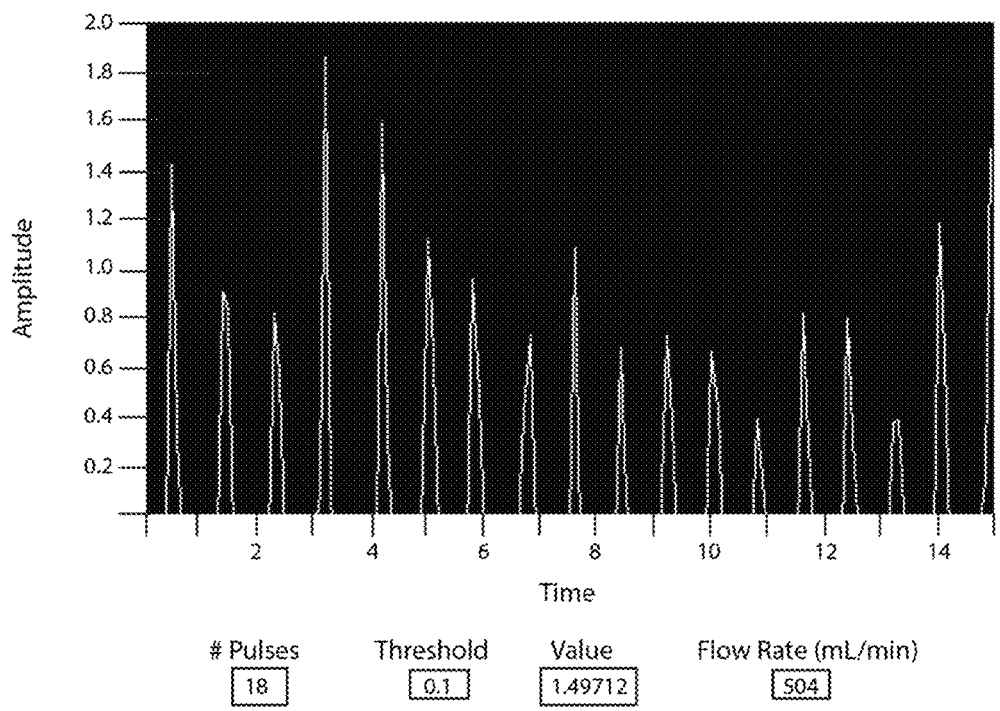
FIG. 10 is a waveform graph of finished signal processing with distinct pulses, counted at a threshold of 0.1, to establish the flow rate.
FIG. 11 is a chart that indicates how to optimize prototype function by increasing blood volume and sensor distance. (Y=error, detected flow rate−expected flow rate; X0=1; X1=blood volume, 60% filled vs. 80% filled; X2=sensor distance, 2 in vs. 4 in).

The sample rate was set to 1000 Hz to obtain as close to a continuous reading from the instrumentation amplifier as possible. Initially, every sample was plotted. In order to obtain less noisy results, the sample number was changed to 100, and the mean of the 100 samples would be plotted. Therefore, a new point appeared every 0.1 second. The resulting graph was FIG. 8 which exhibits data over 15 seconds that has clear, easily recognizable peaks. Higher sample numbers were tested, but proved to be less representative of the applied force as they would miss fast pulses. FIG. 9 shows a single pulse with every sample plotted. FIG. 10 shows signal from the final LabVIEW code with pulse count, threshold values, and flow rate calculations. FIG. 10 is a waveform graph of finished signal processing with distinct pulses, counted at a threshold of 0.1, to establish the flow rate.

The final LabView output counts the number of pulses and calculates average flow rate over a 15 second period. Additionally, it exhibits danger of low flow rates via a boolean light that lights up when the flow rate is below 500 ml/min. The flow rate is calculated using literature values that indicate that the heart ejects 70 ml/beat and that the kidneys receive 20-25% of blood flow. Therefore, amount of blood per pulse can be calculated, summed, and averaged given the 15 second period. The virtual instrument gives a continuous reading of the pressure applied by the renal artery, through which an updated flow rate can be displayed every 15 seconds. The Labview signal processing software also calculates the amount of blood and the given blood pressure at any instantaneous point in time and measures heart rate (e.g. heart beats per minute).

Figure 13:
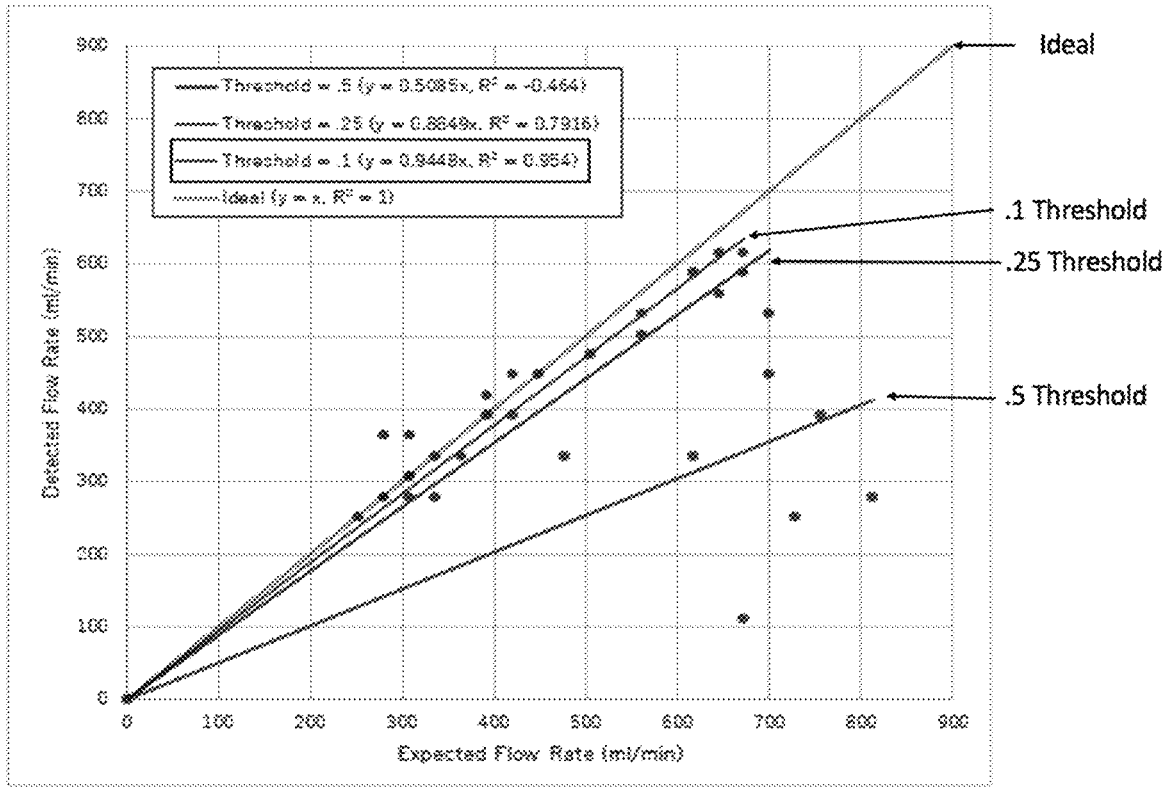
FIG. 13 is a graph showing flow rate modeling with different thresholds (optimization of threshold value)

In this section, we were testing whether or not we could accurately calculate flow rate from pressure readings. To do this, we needed to count the number of pulses being displayed on the LabView Waveform generator graph. FIG. 13 (with threshold lines) shows signals from the renal artery and our set threshold numbers.

After the signal processing in Section 4.1 had been completed, distinct peaks were plotted on the Labview Graph whenever pressure was applied to the pressure transducer. However, as can be seen in FIG. 10, these peaks varied greatly in amplitude. Thus, background noise became a concern that we wanted to minimize. In order to make sure that the peaks that were being counted were actual peaks caused by a pulsing event, different peak threshold levels were tested. Anything above a set threshold would be counted as a true peak, and anything below would be discarded. For the results, each of the graphs display data from the three thresholds shown in FIG. 13. The threshold that allowed for the most accurate digital representation of the applied flow rate was selected for the final prototype design.

As the threshold was lowered from 0.5 to 0.1, the accuracy of the pulsation detection increased. This can be seen in the trendline equations where the slope goes from 0.1208 for the 0.5 threshold to 0.9664 for the 0.1 threshold. For perfect accuracy, we would expect the slope of the trendline to be at 1, thus the 0.1 threshold was the most accurate of those tested. This can be seen in FIG. 13. Using the pulses detected, we then calculated the flow rate we expected given the number of pulses applied and compared it to the flow rate calculate from the LabView code. Additionally, since the flow rate can never be negative, we forced the trend lines from these data to go through the point (0,0). This resulted in FIG. 13 where the x-axis is the expected flow rate and the y-axis is the flow rate the LabView code calculated.

In another area of our LabView code, we set a detection system that would turn on a red light if the measured flow rate was below 500 mL/min, indicating kidney failure or thrombosis. For each of the thresholds, we recorded not only what the pulses counted and the predicted flow rate was, but also whether or not this light turned on for a specific trial. The y-axis for this graph is the actual flow rate that was applied to the pressure transducer, not the LabView calculated flow rate. For a perfect detection system, all the points above the dotted line at 500 mL/min would be green and all the points below it would be red. As the threshold for peak detection was lowered, the number of points falsely colored red lowered.

The clamping mechanism serves a twofold purpose. To begin, it must hold the device components in place to ensure accurate pressure transducer readings. This means the transducer must be continually pressed up against the renal artery and not change position. The second purpose of the clamp is to enable the safe removal of the device at the bedside, without the need for another invasive procedure.

Figure 2:
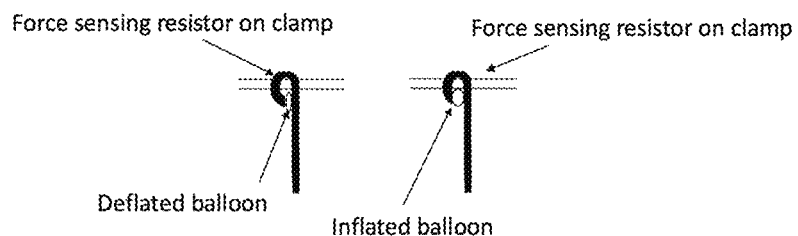
FIG. 2 depicts a non-invasive clamp removal method utilizing an inflating balloon mechanism to release and remove the clamp and the Force Sensing Resistor (FSR) from the renal artery.
Figure 3:
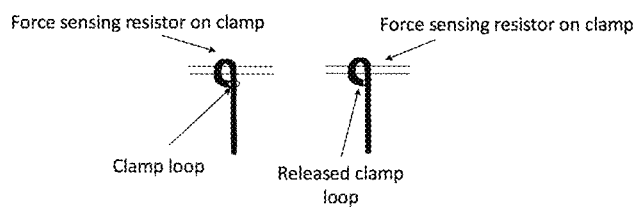
FIG. 3 depicts a minimally invasive method for removing the clamp and the FSR by cutting a clamp loop to release the clamp from the renal artery.
Figure 4:
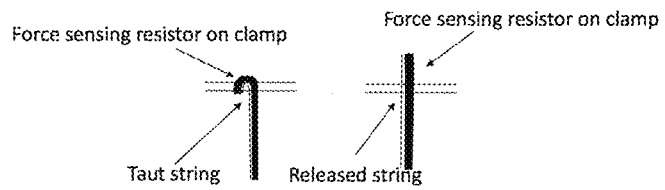
FIG. 4 depicts a non-invasive method of cutting a tight string that will release the clamp from the renal artery and allow for removal of the clamp and the FSR.

FIG. 2-4 shows three different designs for how the clamping mechanism could work (string, balloon, loop). The string mechanism shown in FIG. 4 would work based off of a Lone-Star Retractor system. In this mechanism, a taut string attached to the end of the clamp keeps the hook shape in place around the artery. Once it is cut, the hook shape relaxes and the device can be removed. This design proved to be too difficult to make at the prototype scale we were working with. Additionally, it also limited the amount of surface area that the sensor could have against the artery.

The design shown in FIG. 2 is the closest to the final design. The difference, however, is the placement of the catheter balloon. In this design, the clamp allows for the maximum amount for arterial surface area to be in contact with the sensor which makes it more ideal than the string clamp mechanism because it would probably increase the accuracy of the readings from our device. In order to remove the clamp in this design, the inflation of the catheter balloon causes the clamp to release from the artery. This could be done by having a latch-type mechanism above the balloon that holds the clamp in place. When the balloon inflates, it would lift the latch up and allow for the clamp to be released.

The last design considered is shown in the last panel of FIG. 3. In this design, the clamp is attached in a slip-knot mechanism. This would not only allow the maximum amount of the arterial surface area to contact the sensor but would also allow the diameter of the clamp to easily change with the pulsing of the artery. For this clamping mechanism to work, it would have to be made out of an elastic material that could stretch a little as the artery pulsed. If the artery's diameter increased to a degree that the elastic material could not stretch, the slip knot mechanism would allow the closed loop to slide down and open up the loop around the artery more. This design was conceptualized in order to try to account for the fact that the artery can change in size as it pulses which could present a problem.

Figure 12:
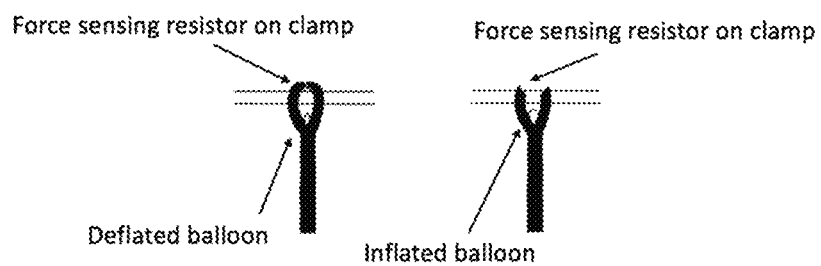
FIG. 12 depicts a clamp design, with the contact between sensory and artery being semi-circular (variables: size, infill %, layer depth). The clamp design includes a small balloon attached to the hinge joint of the clamp. The clamp is attached to the force sensing resistor for blood pressure measurement of the renal artery.

FIG. 12 depicts a clamp design, with the contact between sensor and artery being semi-circular. The clamp design includes a small balloon attached to the hinge joint of the clamp. The clamp is attached to the force sensing resistor for blood pressure measurement of the renal artery. The clamp design consisted of two parts: (1) the top, where the catheter balloon and the renal artery will be put through the two holes, and (2) the base, on which the pressure transducer is sitting directly adjacent to the artery. When the device is ready to be removed, air will be injected into the catheter, which causes the balloon inside to expand rapidly and pull the hinged top off the artery in the process. The balloon will then be deflated and the device will be safely pulled out of the patient.

The design is optimal because of its shape and the minimized contact angle between the sensor and the artery at various points during blood flow. To begin, this design has a semicircular shape, which we found was the best shape to get the most accurate pressure transducer readings and allow the artery to expand as much as it needs to during blood flow. Furthermore, the contact between the pressure transducer and the artery is maximized when the artery is in the latter stage of blood flow, allowing for better pressure transducer readings that are able to differentiate between different arterial flow rates.

Three variables had to be optimized during the 3D printing step of the final design. To begin, the size of the device had to be accurate in order to fit the dimensions of the pressure transducer, dialysis tubing, and catheter. We first made one iteration of the device with roughly measured dimensions. From this model, we found that the base was too long will the base did not extend far enough to form the clamping structure. Based on these results, we iteratively changed the dimensions in a Solidworks file until the parts fit together correctly.

Furthermore, the infill percentage and layer height used while 3D printing could be varied to yield structures of varying stiffnesses and structural properties. These variables had to be accounted for because the clamp could not be so stiff that the force exerted by the expansion of the catheter balloon was not sufficient to pull it off the artery. We started with a layer height of 0.1 mm and an infill percentage of 10%. Upon testing, we found that these values were optimal because the clamp was sturdy enough to keep the device components in place but still able to be moved due to the catheter balloon.

Two additional variables to consider in our model were: (1) the volume of blood and (2) where along the tubing we performed our pressure measurements. An orthogonal design analysis was used to determine each variable's relative effect on our model of the artery. FIG. 11 depicts is the test matrix used for these tests. Two blood volumes were tested: 60% full (−1) and 80% full (1). The two distances indicate the distance of the left end of the dialysis tubing from the left end of the sensor, 2 inches (−1) and 4 inches (1). For each test, we applied 15 pulses over 15 seconds which equates to a flow rate of 420 ml/min. We then measured the output flow rate from our device and subtracted the expected flow rate from the detected flow rate.

Using a first order model, $Y=B0*X0+B1*X1+B2*X2$, where $X0=1$, $X1=$Blood Volume, $X2=$Distance, $Y=$Error, the resulting model is $Y=17.5*X0-17.5*X1+17.5*X2$. This indicates that both blood volume and distance affect the amount of error relatively equally, but in opposite ways. Increased blood volume decreases error while increased sensor distance increases error.

One embodiment includes a real-time kidney monitoring apparatus, comprising: a force sensing resistor configured to wrap around a renal artery of a kidney; and a clamp to hold the force sensing resistor to the renal artery.

Some example implementations include the force sensing resistor is a pressure transducer, the resistance of the pressure transducer decreases in response to applied pressure.

Some example implementations further comprise a monitoring circuit connected to the force sensing resistor; and a computer connected to the monitoring circuit, the computer includes signal processing software that calculates a blood flow metric for the renal artery.

Some example implementations include the monitoring circuit includes a wheatstone bridge; the force sensing resistor is part of the wheatstone bridge; the monitoring circuit includes an operational amplifier; two legs of the wheatstone bridge are connected to two inputs of the operational amplifier which amplifies the difference between the two inputs, an output voltage of the operational amplifier is sent to the computer and the signal processing software.

Some example implementations include that the three resistors in the wheatstone bridge have a common resistance that is chosen to be close to the a resting resistance of the force sensing resistor so when no force is applied to the force sensing resistor by the renal artery then the two legs have a same voltage and the operational amplifier does not have a significant voltage differential to amplify.

Some example implementations further comprise a monitoring circuit connected to the force sensing resistor; and a computer connected to the monitoring circuit, the computer includes signal processing software that calculates the amount of blood and the given blood pressure at any instantaneous point in time, and measures heart rate.

Some example implementations further comprise a monitoring circuit connected to the force sensing resistor; a computer connected to the monitoring circuit; and a monitor connected to the computer, the monitor configured to provide alerts if irregular kidney function should occur.

Some example implementations include the apparatus is biocompatible, sterile, easily removed from the renal artery, and smaller than 5 mm in diameter.

One embodiment includes a real-time kidney monitoring apparatus, comprising: a force sensing resistor configured to sense a renal artery of a kidney; and a clamp to hold the force sensing resistor to the renal artery.

In some example implementations, the clamp comprises a taut string.

In some example implementations, the clamp comprises a catheter balloon.

In some example implementations, the clamp comprises a slip-knot mechanism with elastic material that could stretch.

In some example implementations, the clamp comprises a balloon attached to the hinge joint.

Some example implementations further comprise a monitoring circuit connected to the force sensing resistor; and a computer connected to the monitoring circuit, the computer includes signal processing software that calculates a blood flow metric for the renal artery.

In some example implementations, resistance of the force sensing resistor is indicative of blood flow through the renal artery of the kidney.

One embodiment includes a real-time kidney monitoring apparatus, comprising: a pressure transducer configured to sense a renal artery of a kidney; and a clamp to hold the pressure transducer against the renal artery.

In some example implementations, the pressure transducer is flexible.

In some example implementations, the pressure transducer is printed on silicone.

In some example implementations, the pressure transducer is biocompatible.

Some example implementations further comprise a monitoring circuit connected to the pressure transducer; and a computer connected to the monitoring circuit, the computer includes signal processing software that calculates a blood flow metric for the renal artery; the pressure transducer is flexible, printed on silicone and is biocompatible.

For purposes of this document, reference in the specification to "an embodiment," "one embodiment," "some embodiments," or "another embodiment" may be used to describe different embodiments or the same embodiment.

For purposes of this document, a connection may be a direct connection or an indirect connection (e.g., via one or more others parts). In some cases, when an element is referred to as being connected or coupled to another element, the element may be directly connected to the other element or indirectly connected to the other element via intervening elements. When an element is referred to as being directly connected to another element, then there are no intervening elements between the element and the other element. Two devices are "in communication" if they are directly or indirectly connected so that they can communicate electronic signals between them.

For purposes of this document, the term "based on" may be read as "based at least in part on."

For purposes of this document, without additional context, use of numerical terms such as a "first" object, a "second" object, and a "third" object may not imply an ordering of objects, but may instead be used for identification purposes to identify different objects.

For purposes of this document, the term "set" of objects may refer to a "set" of one or more of the objects.

The foregoing detailed description has been presented for purposes of illustration and description. It is not intended to be exhaustive or to limit to the precise form disclosed. Many modifications and variations are possible in light of the above teaching. The described embodiments were chosen in order to best explain the principles of the proposed technology and its practical application, to thereby enable others skilled in the art to best utilize it in various embodiments and with various modifications as are suited to the particular use contemplated. It is intended that the scope be defined by the claims appended hereto.

What is claimed is:

1. A real-time kidney monitoring apparatus, comprising:
   a force sensing resistor configured to wrap around a renal artery of a kidney;
   a clamp configured to hold the force sensing resistor to the renal artery;
   a monitoring circuit connected to the force sensing resistor; and
   a computer connected to the monitoring circuit, the computer includes signal processing software that is configured to calculate a blood flow metric for the renal artery, the monitoring circuit includes a wheatstone bridge, the force sensing resistor is part of the wheatstone bridge, the monitoring circuit includes an operational amplifier, two legs of the wheatstone bridge are connected to two inputs of the operational amplifier which amplifies the difference between the two inputs, an output voltage of the operational amplifier is provided to the computer and the signal processing software;
   three resistors in the wheatstone bridge have a common resistance that is chosen to be close to a resting resistance of the force sensing resistor so when no force is applied to the force sensing resistor by the renal artery then the two legs have a same voltage and the operational amplifier does not have a significant voltage differential to amplify.

2. The real-time kidney monitoring apparatus of claim 1, further comprising:
   a monitor connected to the computer, the monitor is configured to provide an alert if irregular kidney function is sensed by the force sensing resistor.

3. The real-time kidney monitoring apparatus of claim 1, wherein:
   the signal processing software is configured to calculate amount of blood and blood pressure at any instantaneous point in time, and measures heart rate.

4. The real-time kidney monitoring apparatus of claim 1, wherein:
   the signal processing software is configured to calculate amount of blood and blood pressure.

* * * * *